US006869281B2

(12) United States Patent
Doviack

(10) Patent No.: US 6,869,281 B2
(45) Date of Patent: Mar. 22, 2005

(54) TOOTH MODEL OCCLUSION TESTING DEVICE

(76) Inventor: Jerry W. Doviack, 9510 S.La Cienega Blvd., Inglewood, CA (US) 90301

( * ) Notice: Subject to any disclaimer, the term of this patent is extended or adjusted under 35 U.S.C. 154(b) by 58 days.

(21) Appl. No.: 10/337,291

(22) Filed: Jan. 7, 2003

(65) Prior Publication Data

US 2004/0131990 A1 Jul. 8, 2004

(51) Int. Cl.[7] .............................................. A61C 11/00
(52) U.S. Cl. ............................. 433/60; 433/57; 433/55
(58) Field of Search ............................. 433/60, 61, 66, 433/54, 196, 34, 58, 56, 68, 55, 50, 59, 57

(56) References Cited

U.S. PATENT DOCUMENTS 5,366,373 A * 11/1994 Mumolo et al. .............. 433/58
5,425,636 A * 6/1995 Ghim ........................... 433/64
5,494,440 A * 2/1996 Silva et al. .................... 433/58

* cited by examiner

Primary Examiner—Melba Bumgarner
(74) Attorney, Agent, or Firm—Birch, Stewart, Kolasch & Birch, LLP.

(57) ABSTRACT

A tooth model occlusion testing device comprises an upper jaw and a lower jaw that pivotally connect to each other. Two tooth model bases are respectively received in the upper and lower jaws, and are provided with a plurality of perforations to insert a tooth model. The upper and lower jaws are thereby capable of turning to an open and occluding position to evaluate the alignment of the upper and lower parts of the tooth model in the occluding position.

15 Claims, 6 Drawing Sheets

TOOTH MODEL OCCLUSION TESTING DEVICE

FIELD OF THE INVENTION

The invention relates to a tooth model occlusion testing device and, more particularly, to a tooth model occlusion testing device that is reusable.

BACKGROUND OF THE INVENTION

Dental caries are usually cured by fill of amalgams. However, when the dental caries are too serious, tooth extraction then is necessary. To replace the extracted tooth, an artificial tooth may be constructed and mounted at the corresponding location of the extracted tooth. To construct the artificial tooth, the shape of the damaged tooth is impressed in a tooth mold before it is extracted. A tooth model then is obtained from the tooth mold. Once achieved, the tooth model is usually placed in a tooth model occlusion testing socle and is returned to the dentist to confirm that there is no defect on the tooth model. Thereafter, the artificial tooth can be constructed from the tooth model.

As illustrated in FIG. 1, the conventional tooth model occlusion testing socle comprises an upper base 81 and a lower base 82 that pivotally connect to each other. The upper and lower bases 81, 82 respectively include a plurality of perforations 83, 84 to insert the tooth model (not shown).

However, the above tooth model occlusion testing socle has the following inconveniences.

(1) The upper and lower bases are designed with the tooth model bases in a single body. This results in an inconvenient manufacturing process and, furthermore, may cause damages of the testing socle when the testing socle and the tooth model are together returned to the dentist.

(2) After the artificial tooth is fabricated from the tooth model, the tooth model occlusion testing socle is usually thrown away. This constitutes a waste of material and, furthermore, may cause environmental pollution because the tooth model occlusion testing socle is usually made of plastics materials that do not easily decompose naturally.

(3) The conventional tooth model occlusion testing socle usually is roughly fabricated, so that the testing socle is not securely positioned in the open and occluding positions. This results in higher chances of damage of the testing socle, and further may affect the precision in evaluating the alignment of the tooth model in the occluding position.

SUMMARY OF THE INVENTION

Accordingly, it is a principal object of the invention to provide a tooth model occlusion testing device that allows a convenient use and is reusable a plurality of times.

To achieve the above and other objectives, a tooth model occlusion testing device of the invention comprises an upper jaw and a lower jaw that pivotally connect to each other. Two tooth model bases, provided with a plurality of perforations, are respectively mounted to the upper and lower jaws to assemble a tooth model. The tooth model occlusion testing device is thereby capable of turning to an open and occluding position to evaluate the alignment of the tooth model in the occluding position.

To provide a further understanding of the invention, the following detailed description illustrates embodiments and examples of the invention, this detailed description being provided only for illustration of the invention.

BRIEF DESCRIPTION OF THE DRAWINGS

The drawings included herein provide a further understanding of the invention. A brief introduction of the drawings is as follows.

DETAILED DESCRIPTION OF THE EMBODIMENTS

Figure 1:
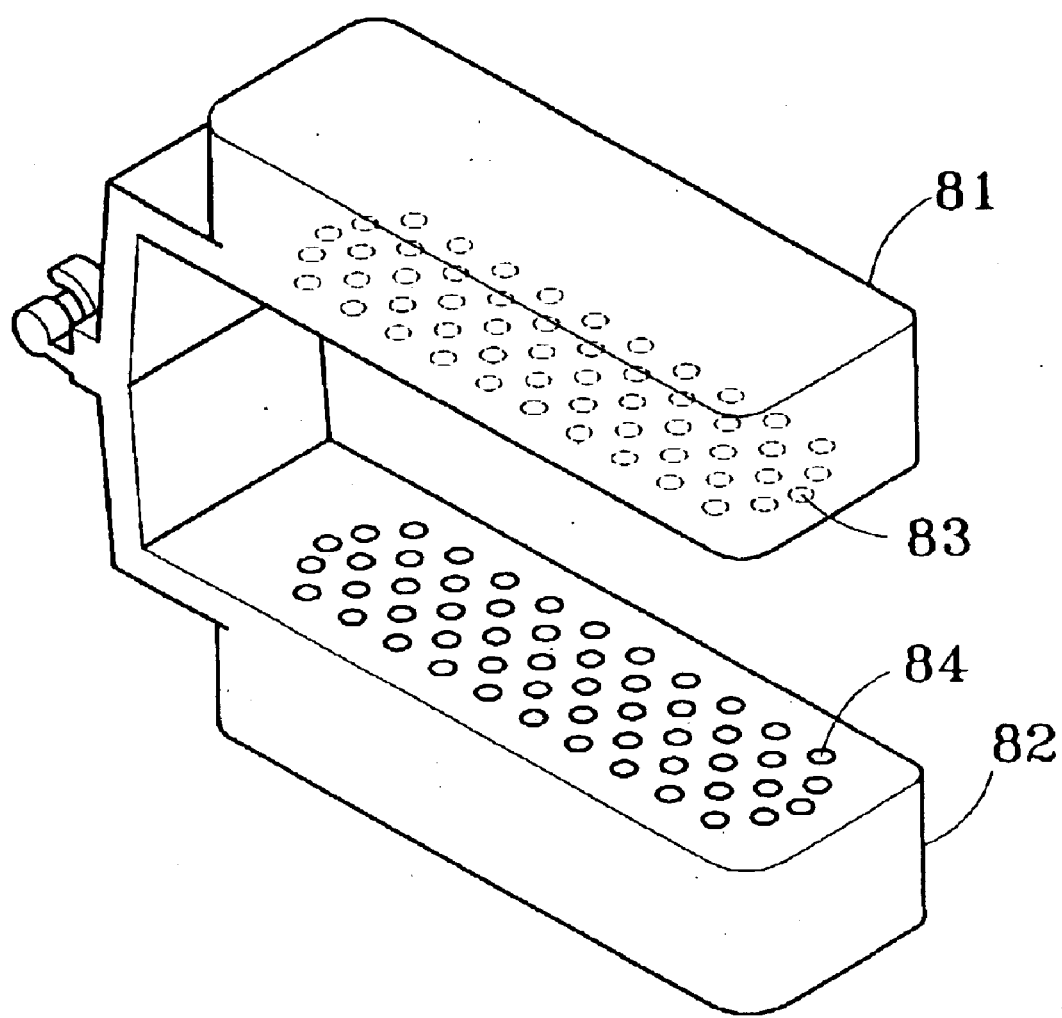
FIG. 1 is a perspective view schematically illustrating a tooth model occlusion testing socle of the prior art.

Wherever possible in the following description, like reference numerals will refer to like elements and parts unless otherwise illustrated.

Figure 2:
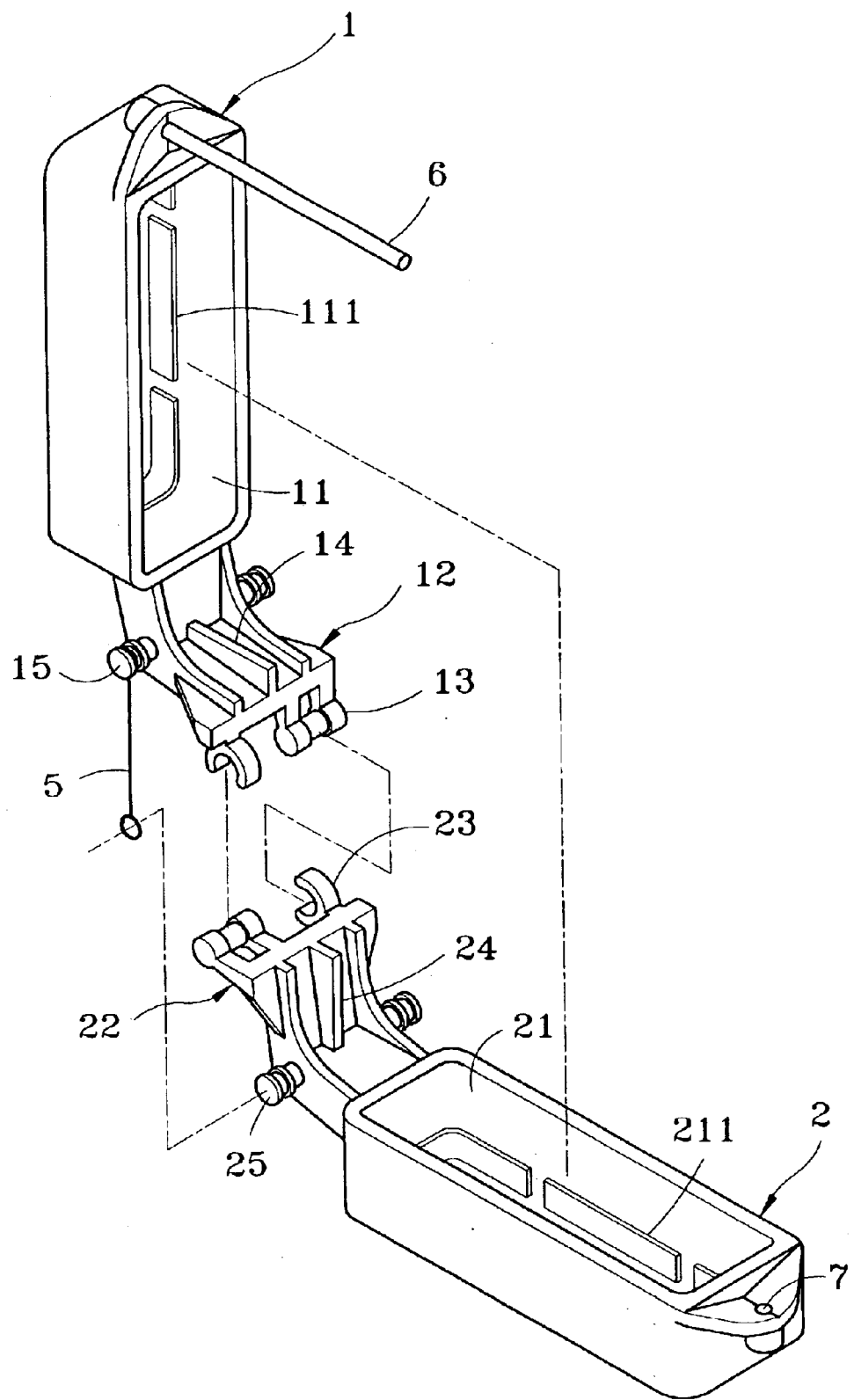
FIG. 2 is an exploded view schematically illustrating a tooth model occlusion testing device according to an embodiment of the invention.

Referring to FIG. 2, an exploded view schematically illustrates an embodiment of the invention. A tooth model occlusion testing device of the invention comprises an upper jaw 1, a lower jaw 2, and a resilient element 5. The upper and lower jaws 1, 2 pivotally connect to each other so as to receive the bases of an upper part and lower part of a tooth model (not shown) and test whether they occlude in alignment.

The upper jaw 1 comprises a placement cavity 11 dedicated to the reception of the tooth model base of an upper part of the tooth model (not shown). An inner sidewall of the placement cavity 11 includes a projection 111. One side of the upper jaw 1 terminates in an arm 12 while an opposite side of the upper jaw 1 includes a positioning rod 6 used to fixedly position the upper and lower jaws 1,2 relative to each other. One side of the arm 12 has a hinge 13 through which are pivotally connected the upper and lower jaws 1,2. At the same side of the hinge 3.3 is provided an abutment 14 by means of which the upper and lower jaws 1,2 are securely positioned relative to each other in open or occlusion configurations.

The lower jaw 2 includes a placement cavity 21 dedicated to the reception of the tooth model base of a lower part of the tooth model (not shown). An inner sidewall of the placement cavity 21 includes a projection 211. One side of the lower jaw 2 terminates in an arm 22 while an opposite side of the lower jaw 2 has a positioning finger 7 corresponding to the positioning rod 6. When the upper jaw 1 is turned to an occlusion position over the lower jaw 2, the positioning rod 6 abuts against the positioning finger 7. One side of the arm 22 has a hinge 23 through which the upper and lower jaws 1, 2 are pivotally connected to each other. An abutment 24 is provided on the same side of the hinge 13 to securely position the upper and lower jaws 1, 2 relative to each other in open and occlusion configurations.

The resilient element 5 is mounted on the upper and lower jaws 1, 2 by means of retainer projections 15, 25 respectively provided on the upper and lower jaws 1, 2. The resilient element 5 is, for example, an elastic string or a spring with flexible characteristics that allow the tooth model occlusion testing device, when operated for opening or closing, to remain securely fastened with each other.

Figure 3:
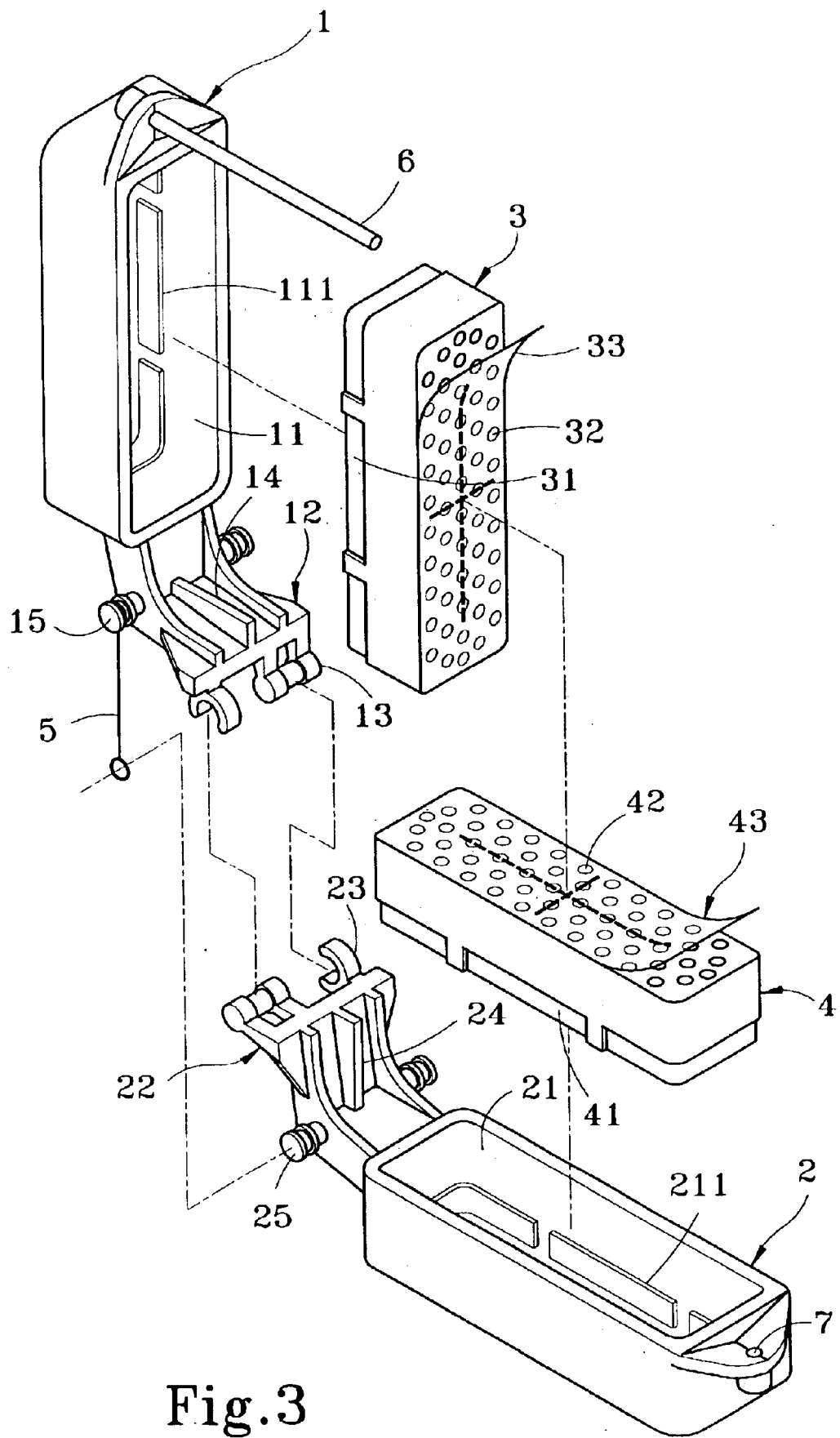
FIG. 3 is an exploded view schematically illustrating a tooth model occlusion testing device according to another embodiment of the invention.
Figure 4:
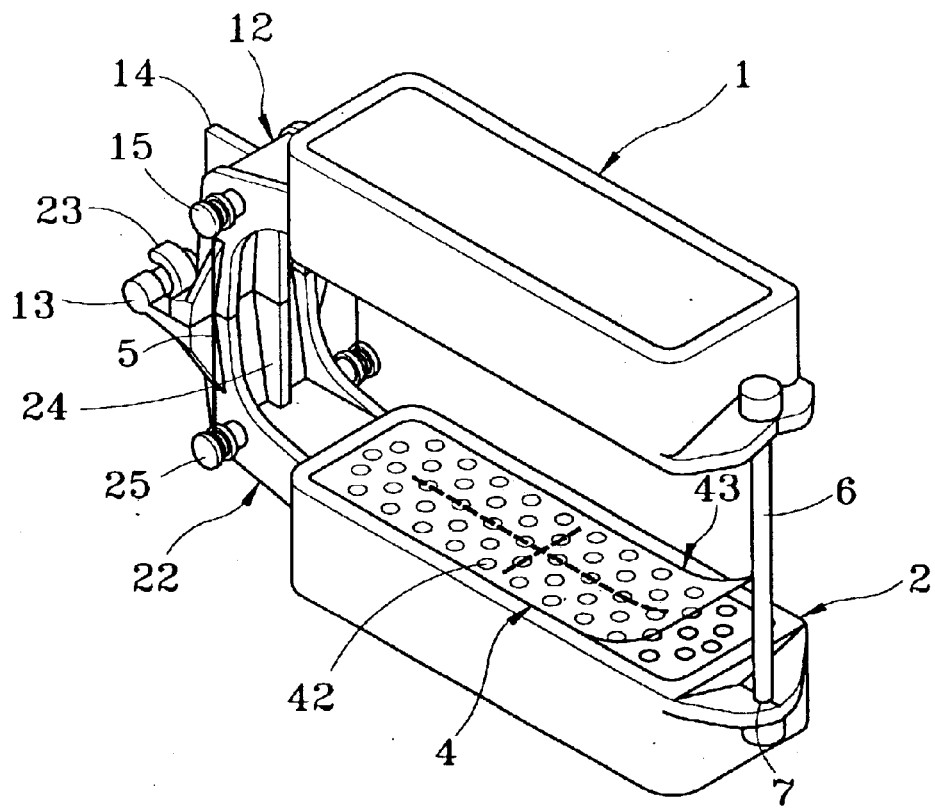
FIG. 4 is a perspective view schematically illustrating an assembled tooth model occlusion testing device of the invention.

Referring to FIG. 3 and FIG. 4, an exploded view and an assembly perspective view schematically illustrates another embodiment of the invention. As illustrated, the tooth model occlusion testing device of the invention may further comprises two tooth model bases 3, 4 that are respectively received in the placement cavities 11,21. The tooth model bases 3, 4 respectively include recessed portions 31,41 that correspondingly engage with the projections 111,211 of the inner sidewalls of the cavities 11, 21 to securely position the tooth model bases 3, 4 in the upper and lower jaws 1, 2. A surface of each of the tooth model bases 3, 4 further respectively includes a plurality of perforations 32, 42 to insert the corresponding tooth models (not shown). On each of the tooth model bases 3, 4 may be further respectively adhered transparent films 33, 43 that are marked with central reference indicator lines and rear and front direction indicator lines. These films 33, 43 are changed after each use to keep an adequate hygiene of utilization.

Figure 5A:
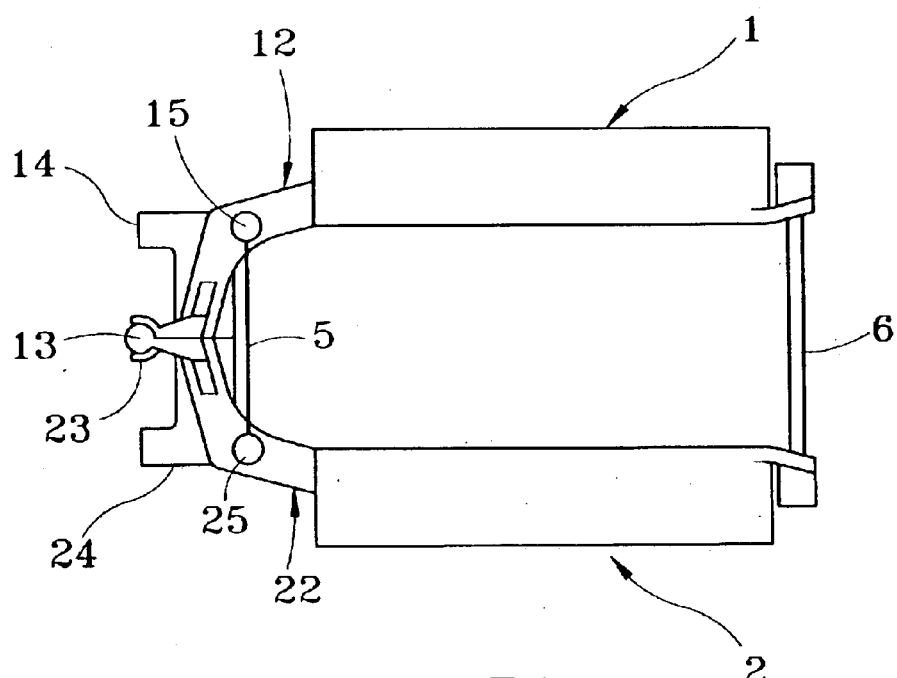
FIG. 5A and FIG. 5B are schematic views illustrating the operation of the tooth model occlusion testing device of the invention.
Figure 5B:
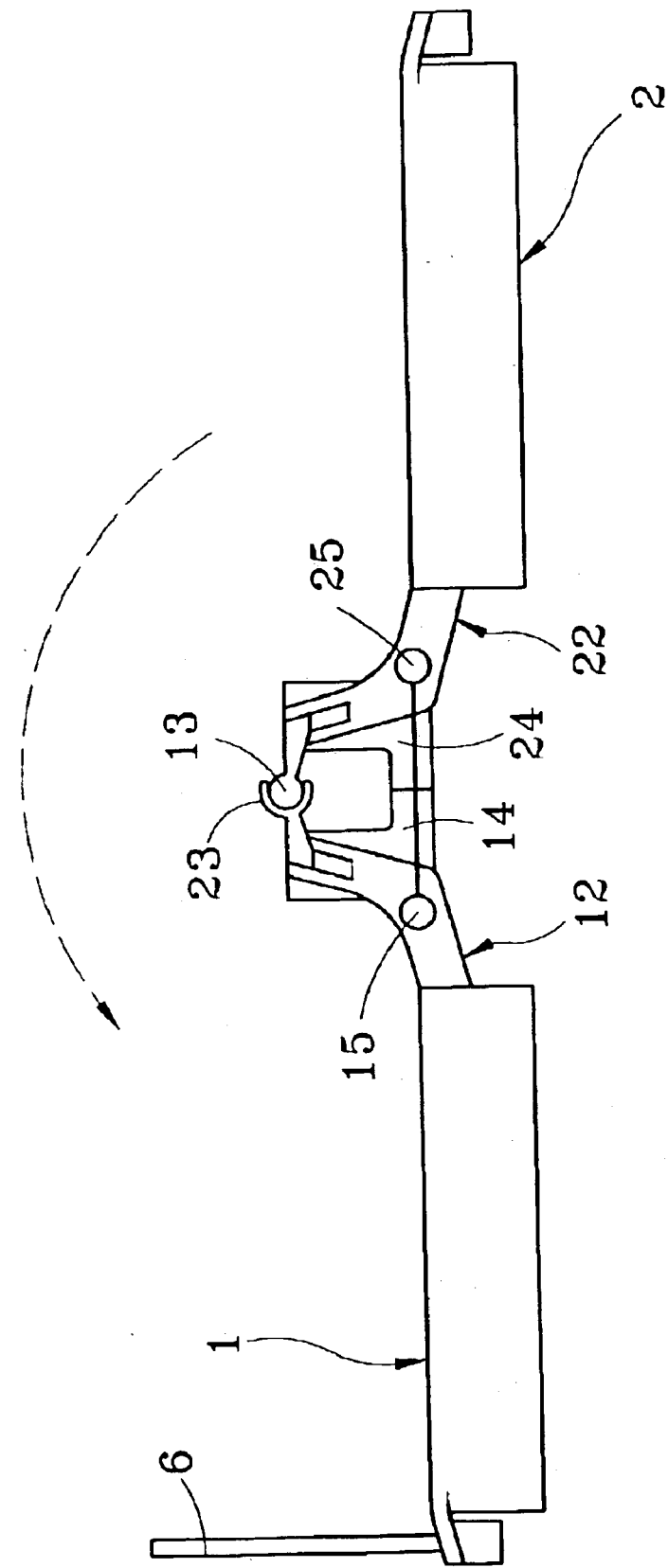

Referring to FIG. 5A and FIG. 5B, two schematic views illustrate the operations of the embodiment of the invention. As described above, the upper and lower jaws 1, 2 pivotally connect to each other via the hinges 13, 23. In an open configuration, the abutments 14, 24 abut against each other and through the action of the resilient element 5, the upper and lower jaws 1, 2 are securely positioned relative to each other (see FIG. 5B). In an occlusion configuration, the abutments 13, 23 on the other side abut against each other and the positioning rod 6 abuts against the positioning finger 7. Via the resilient element 5, the upper and lower jaws 1,2 are securely positioned in an occlusion position to evaluate whether the upper and lower parts of the tooth model achieve an aligned occlusion.

Figure 6:
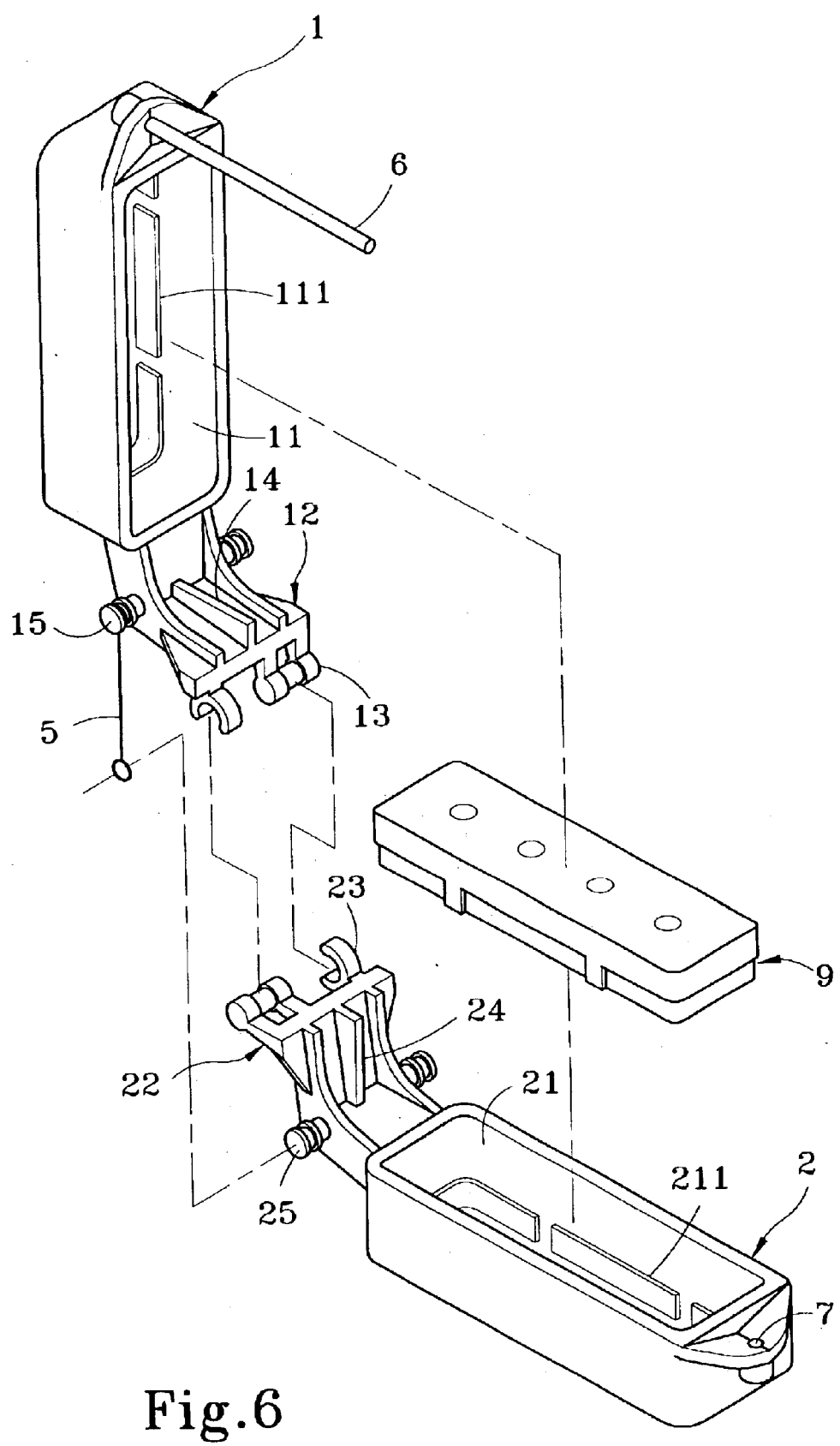
FIG. 6 is an exploded view schematically illustrating a tooth model occlusion testing device according to another variant embodiment of the invention.

Referring to FIG. 6, the tooth model bases 3, 4 may be possibly replaced with a single insert 9 relatively thinner to reduce the material cost.

Those skilled in the art will readily appreciate that the above description is only illustrative of specific embodiments and examples of the invention. The invention should therefore cover various modifications and variations made to the structure of the invention described herein, provided they are included within the scope of the invention as defined in the following appended claims.

What is claimed is:

1. A tooth model occlusion testing device, used to test the alignment of an upper part and a lower part of a tooth model in an occlusion configuration, the testing device comprising:

an upper jaw, including a first placement cavity where is received the upper part of the tooth model, one side of the upper jaw terminating in a first arm that has a first hinge;

a lower jaw, including a second placement cavity where is received the lower part of the tooth model, one side of the lower jaw terminating in a second arm that has a second hinge, the upper and lower jaws pivotally connecting to each other via the first and second hinges, thereby the upper and lower jaws are capable of turning to open and occluding positions to evaluate the alignment of the upper and lower parts of the tooth model in the occluding position; and two tooth model bases, respectively received in the first and second placement cavities, the tooth model bases respectively including a plurality of perforations to respectively insert the upper and lower parts of the tooth model; and a plurality of transparent films, respectively adhered on the tooth model bases, the transparent films being marked with central reference indicator lines and front and rear direction indicator lines, thereby the upper and lower jaws are capable of turning to the open and occluding position to evaluate the alignment of the upper and lower parts of the tooth model in the occluding position.

2. The device of claim 1, wherein the upper and lower jaws at a same side of the first and second hinges further respectively include first and second abutments for relatively positioning the upper and lower jaws in the open and occluding positions.

3. The device of claim 1, wherein the upper and lower jaws at a same side of the first and second hinges further respectively include retainer projections on which is securely held a resilient element.

4. The device of claim 3, wherein the resilient element is provided with resilient characteristics that allow to securely fasten the upper and lower jaws in the open and occluding positions.

5. The device of claim 1, wherein the upper and lower jaws at a side opposite to that of the first and second arms are respectively provided with a positioning rod and a positioning finger that abut against each other when the upper and lower jaws are in the occluding position.

6. A tooth model occlusion testing device, used to test the alignment of an upper part and a lower part of a tooth model in an occlusion configuration, the testing device comprising:

an upper jaw, including a first placement cavity, one side of the upper jaw terminating in a first arm that has a first hinge;

a lower jaw, including a second placement cavity, one side of the lower jaw terminating in a second arm that has a second hinge, the upper and lower jaws pivotally connecting to each other via the first and second hinges;

at least one tooth model base received in one of the first and second placement cavities, the tooth model base including a plurality of perforations to insert one of the upper and lower parts of the tooth model; and a transparent film adhered on the tooth model base, the transparent film being marked with central reference indicator lines and front and rear direction indicator lines.

7. The device of claim 6, wherein the tooth model base is integrated in a single thin insert.

8. The device of claim 6, wherein the at least one tooth model base includes two tooth model bases, one of the tooth model bases being insertable into the upper part of the tooth model and the other of the tooth model bases being insertable into the lower part of the tooth model, thereby the upper and lower jaws are turnable to open and occluding positions to evaluate alignment of the upper and lower parts of the tooth model in the occluding position.

9. The device of claim 8, wherein an inner sidewall of each of the first and second placement cavities and each of the tooth model bases are further respectively provided with corresponding projections and recessed portions to adequately position the tooth model bases in the first and second placement cavities.

10. The device of claim 8, wherein each of the tooth model bases has a transparent film adhered thereto.

11. A tooth model occlusion testing device, used to test the alignment of an upper part and a lower part of a tooth model in an occlusion configuration, the testing device comprising:

an upper jaw, including a first placement cavity, one side of the upper jaw terminating in a first arm that has a first hinge;

a lower jaw, including a second placement cavity, one side of the lower jaw terminating in a second arm that has a second hinge, the upper and lower jaws pivotally connecting to each other via the first and second hinges;

two tooth model bases, respectively received in the first and second placement cavities, the tooth model bases respectively including a plurality of perforations to respectively insert the upper and lower parts of the tooth model; and a plurality of transparent films, respectively adhered on the tooth model bases, the transparent films being marked with central reference indicator lines and front and rear direction indicator lines, thereby the upper and lower jaws are capable of turning to open and occluding positions to evaluate the alignment of the upper and lower parts of the tooth model in the occluding position.

12. The device of claim 11, wherein the upper and lower jaws at a same side of the first and second hinges further respectively include first and second abutments for relatively positioning the upper and lower jaws in the open and occluding positions.

13. The device of claim 11, wherein the upper and lower jaws at a same side of the first and second hinges further respectively include retainer projections on which is securely held a resilient element.

14. The device of claim 13, wherein the resilient element is provided with resilient characteristics that allow to securely fasten the upper and lower jaws in the open and occluding positions.

15. The device of claim 11, wherein the upper and lower jaws at a side opposite to that of the first and second arms are respectively provided with a positioning rod and a positioning finger that abut against each other when the upper and lower jaws are in the occluding position.

* * * * *